United States Patent [19]

Buheitel

[11] Patent Number: 6,165,453

[45] Date of Patent: *Dec. 26, 2000

[54] HAIR CARE AND CONDITIONING PREPARATION AND ITS USE

[75] Inventor: Horst Buheitel, Rehau, Germany

[73] Assignee: Wella Aktiengesellschaft, Darmstadt, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/852,542

[22] Filed: May 7, 1997

Related U.S. Application Data

[63] Continuation of application No. PCT/EP96/03215, May 7, 1997, abandoned.

[30] Foreign Application Priority Data

Sep. 9, 1995 [DE] Germany ............... 195 33 386
Oct. 19, 1995 [DE] Germany ............... 195 38 901

[51] Int. Cl.⁷ .................. A61K 7/07; A61K 7/06
[52] U.S. Cl. ................. 424/70.1; 424/70.19; 424/74
[58] Field of Search .......... 424/70.1, 74, 70.19

[56] References Cited

U.S. PATENT DOCUMENTS 4,464,400 8/1984 Kimura et al. ............... 424/365
4,592,908 6/1986 Wajaroff et al. ............. 424/70.1
4,938,954 7/1990 Gross et al. ............... 424/71

OTHER PUBLICATIONS

Flick, E. Cosmetic and Toiletry Formulations, P. 430, 1992.

CFTA International Cosmetic Ingredient Dictionary, 4–th Edition, The Cosmetic, Toiletry, and Fragrance Association, Washington, D.C.,J.M. Nikitakis, et al, eds., p.264.(1991).

"A Guide to Formulation Mild Sulfosuccinate Products", published by McIntyre Group Ltd, p. 11.(Jan. 1996).

Primary Examiner—Thurman K. Page
Assistant Examiner—S. Tran
Attorney, Agent, or Firm—Michael J. Striker

[57] ABSTRACT

The hair care and conditioning preparations contains from 65 to 98 percent by weight of a first lipophilic phase, from 33 to 2 percent by weight of a second amphiphilic phase and from 5 to 0 percent by weight water. The first lipophilic phase has one or more conditioning lipophilic active ingredients, preferable jojoba oil, avocado oil, sunflower oil, wheat germ oil, montan wax, mineral wax, petrolatum and/or paraffin and the second amphiphilic phase includes a fatty acid ester, and ethoxylated fatty acid, an exthoxylated fatty acid amine and/or an ethoxylated fatty acid amide, and preferably is polyethoxylated hydrogenated castor oil.

20 Claims, No Drawings

HAIR CARE AND CONDITIONING PREPARATION AND ITS USE

This application is a continuation of PCT application PCT/EP96/003215 now abandoned.,

BACKGROUND OF THE INVENTION

The invention relates to a hair care and conditioning preparation and its use. Such a preparation is understood to mean compositions for improving the general condition of the hair. What it is intended to attain is for instance a soft feel, a glossy appearance, protection against environmental factors and in particular good combability. In its native state or in regions near the roots, the hair still has a closed cuticle, which protects it against drying out but above all against the loss of lipids and against environmental factors; but as the hair ages, which with longer hair can range from months to years, the cuticle becomes increasingly brittle and permeable. The hair dries out and splits. This also makes it more vulnerable to environmental factors. It is known that oils, for instance vegetable oils such as jojoba oil condition the hair or in other words provide a general improvement in its condition, in that particularly in damaged regions of the hair they penetrate the hair or adheres to such regions and in this way improve the general state of the hair and for instance its combability. However, such care and conditioning oils are hard to work into damp hair, especially, and are therefore as a rule not applied pure but rather in the form of oil-in-water emulsions. Such emulsions, however, are not entirely satisfactory in terms of their effectiveness.

SUMMARY OF THE INVENTION

The object of the present invention is therefore to propose a preparation and its use, with which satisfactory care and conditioning of the hair is possible.

The preparation according to the invention contains from 65 to 95 weight % of a first, lipophilic phase and 2 to 23 weight % of a second, amphiphilic phase. The first phase is formed by at least one active care or conditioning substance. The amphiphilic phase is formed by a substance that is selected from a group comprising fatty acids, fatty acid esters, fatty acid amines, and fatty acid amides, each ethoxylated with from 2 to 200 ethylene oxide groups and preferably 5 to 50 ethylene oxide groups and each containing from 6 to 30 carbon atoms.

In contrast to the known oil-in-water emulsions, in the preparation according to the invention, there is no oil-in-water emulsion after shaking but instead an emulsion-like mixture of one lipophilic and one amphiphilic substance acting as a solubilizer. It has now been demonstrated surprisingly that with the mixtures according to the invention, good conditioning of the hair can be attained even though the aqueous phase, which in conventional oil-in-water emulsion-based compositions makes up nearly the bulk of the overall composition, is absent or is present in a proportion of at most 5 weight %. Rinsing after the preparation has been worked in presents no problems, either. Any excess preparation can easily be removed from the hair again with water, possibly with the addition of a shampoo. A water-free preparation preferably contains from 90 to 98 weight % of the active substances and from 2 to 10 weight % of the amphiphilic substance.

As active substances that form the first phase, jojoba oil, avocado oil, sunflower oil, wheat germ oil, montan wax, mineral wax, vaseline and paraffin and mixtures of these substances are preferably used. Especially good results are obtained if the second phase is formed by a polyethoxylated, hydrogenated castor oil. Ricinoleic acid comprises approximately 80 to 85% of a glyceride of the ricinoleic acid as well as glycerides of oleic acid, linoleic acid, palmitic acid and stearic acid. The double bonds of the acid components named are converted by hydrogenation into single bonds; this avoids in particular the development of a film on the hair. By means of the polyethoxylation, a polyethylene glycol is interposed between the glyceride and the respective fatty acid esters. The molecules created in this way are amphiphilic, or in other words have both hydrophilic or hydrophobic regions, and thus act like emulsifiers or solubilizers. However, the preparation according to the invention is not a stable mixture that can be held for a long period of time. The two phases contained in it separate again after only a few minutes. This instability appears to be insignificant for the conditioning action of the preparation according to the invention. An especially advantageous preparation can be obtained if the hydrogenated castor oil is ethoxylated with from 5 to 60 ethylene oxide groups, for instance 7 or 40 ethylene oxide groups. The various glycerides of a castor oil modified in this way then contain on average 7 or 40 ethylene oxide or ethylene glycol groups, for instance. A preparation according to the invention preferably has other care-providing and physiologically favorably acting substances, such as lecithins and vitamins, as well as antioxidants as protection against aging or against oxidative processes.

A preferred preparation comprises 84 weight % jojoba oil and 16 weight % hydrogenated polyethoxylated castor oil.

A further preferred preparation contains 33 weight % jojoba oil, 32 weight % sunflower oil, 31 weight % avocado oil, 2 weight % castor oil ethoxylated with 40 ethylene oxide groups, 1 weight % castor oil ethoxylated with 7 ethylene oxide groups, 0.1 weight % oxidant, and 0.9 weight % water.

The preparation according to the invention is preferably worked into the hair undiluted. The ingredients present in separate phases in the preparation are initially mixed intimately with one another by moving or shaking the preparation. The creates an emulsionlike mixture, in which the hydrophilic phase virtually forms the outer phase. The thoroughly mixed preparation is applied to the damp or wet hair and worked in. The dosage of the preparation may be made in accordance with the particular state of the hair and depending on any prior or subsequent treatment. For instance, badly damaged hair requires a higher dosage than less severely damaged hair. The action time, which as a rule is a few minutes, can also be varied depending on the condition of the hair. Following the action time, the excess preparation is removed again. To do so it suffices merely to rinse with plain water. It is not necessary to add a shampoo in every case. Depending on the hair type and the damage to the hair, it may be advantageous if the application is done at elevated temperature, in particular at 30 to 45° C. During the action time, the hair can be heated with an infrared radiation device, for instance.

In an advantageous use, the preparation according to the invention is applied to the hair as a balancing pre-wrap solution in the course of a permanent shaping process before a permanent shaping composition is applied.

One other possible use is for the preparation to be added to a hair treatment composition before that composition is applied. Hair treatment compositions are understood in general to mean cosmetic and care preparations, such as hair coloring compositions, permanent-waving compositions, instant conditioners, conditioners left on for a longer time, hair lotions, shampoos, hair tonics, setting lotions, hair strengtheners, volumizers, and so forth. The preparation is first shaken, as described above, to bring about an intimate mixture of its ingredients. It is then added to a hair treatment composition, and this composition is then applied to the hair. The proportion of the preparation in the hair treatment composition is at least 5 weight % and preferably at least 10 weight %. In proceeding in this way, although the preparation according to the invention is as described above not used pure, nevertheless satisfactory conditioning of the hair is attained. A substantial advantage both of this procedure and of the separate application of the preparation compared with conventional hair treatment compositions that already contain conditioning additives such as jojoba oil, is that the user is not bound to the content and quantity specifications made by the manufacturer. Instead, he can first ascertain the general condition of the hair of the customer and then undertake an individual dosage. In a particular feature, the preparation according to the invention is packaged together with the hair treatment composition, which is preferably an oxidation-type hair coloring composition, a permanent-waving composition for the first step or a neutralizer for the second step, in a combination packaging unit known as a kit of parts. It is also conceivable that preparations with various ingredients, such as different combinations of active oils, etc., may be kept on hand and selected and dosed individually, that is, depending on the condition and type of hair and the particular hair treatment to be performed at the time. For the uses mentioned, it is advantageous if the user has the components necessary to produce preparations according to the invention on hand in separate packages. For instance, it is conceivable for one or more active ingredients or combinations of active ingredients and suitable solubilizers each to be packed separately. Then not only the dosage of the total preparation but also the quantitative ratio of the active ingredient and solubilizers can be varied.

The invention will now be illustrated in more detail by means of the following examples, the details of which should not be considered as limiting the claims appended hereinbelow.

EXAMPLES

Example 1

Medium-thickness, oxidatively treated hair 20 cm long was washed with a shampoo. Into the hair dried with a towel, 10 ml of a preparation according to the invention, which contained 84 weight % jojoba oil and 16% of a hydrogenated polyethoxylated castor oil with 40 2-hydroxyethyl groups (Cremophor$^{(R)}$ RH40 made by BASF) were worked in. After an action time of 5 minutes, the hair was rinsed with a large amount of water. The hair which previously could be combed only with difficulty, now had considerably improved combability and felt soft and elastic.

Example 2

Normal hair, not treated oxidatively, 25 cm long was washed, and in the towel-dried state, 12 ml of a preparation according to the invention was sprayed on, as a balancing pre-wrap solution of the following composition:

| | |
|---|---|
| 33.0 g | jojoba oil |
| 32.0 g | sunflower oil |

-continued

| | |
|---|---|
| 31.0 g | avocado oil |
| 2.0 g | hydrogenated castor oil ethoxylated with 40 ethylene oxide groups (Cremophor ® RH40 made by BASF) |
| 1.0 g | hydrogenated castor oil ethoxylated with 7 ethylene oxide groups (Arlacel ® 989 made by ICI) |
| 0.1 g | antioxidant |
| 0.9 g | water |
| 100.0 g | |

The balancing pre-wrap solution, first shaken and converted into an emulsionlike mixture, was sprayed on and then worked into the hair by hand and left to act for 5 minutes, and the hair was then rinsed with a great deal of water. In the ensuing permanent shaping operation, a mildly alkaline permanent shaping composition based on ammonium thioglycolate and a neutralizer based on hydrogen peroxide was used.

The application of the preparation took place over the course of a permanent-wave treatment. As a preparatory step, the aforementioned balancing pre-wrap treatment was performed with a preparation according to the invention. The goal of this treatment was to attain a virtually uniform action of the permanent shaping composition over the entire length of the hair. These compositions are known to penetrate more markedly into damaged hair regions than in less severely damaged regions. The preparation according to the invention adheres preferentially to the damaged hair regions; in particular, the active oils contained in it penetrate the layers near the surface of the hair and reduce the active intensity of the permanent shaping composition.

I claim:

1. A hair care and conditioning preparation, consisting essentially of from 65 to 98 percent by weight of a first lipophilic phase, from 2 to 33 percent by weight of a second amphiphilic phase and from 0 to 5 percent by weight water, wherein said first lipophilic phase consists of at least one vegetable-based or animal-based natural oil, and said second amphiphilic phase consists of at least one amphiphilic substance selected from the group consisting of ethoxylated fatty acids, ethoxylated fatty acid amines and ethoxylated fatty acid amides;

wherein said ethoxylated fatty acids are fatty acids containing from 6 to 30 carbon atoms which are ethoxylated with from 2 to 200 ethylene oxide groups; said ethoxylated fatty acid amines are fatty acid amines containing from 6 to 30 carbon atoms which are ethoxylated with from 2 to 200 ethylene oxide groups; and said ethoxylated fatty acid amides are fatty acid amides containing from 6 to 30 carbon atoms which are ethoxylated with from 2 to 200 ethylene oxide groups.

2. The hair care and conditioning preparation as defined in claim 1, wherein said fatty acid amides, said fatty acid amines and said fatty acids are each ethoxylated with from 5 to 50 of said ethylene oxide groups.

3. The hair care and conditioning preparation as defined in claim 1, containing from 90 to 98 weight % of the first lipophilic phase and from 2 to 10 weight % of the second amphiphilic phase.

4. The hair care and conditioning preparation as defined in claim 1, wherein the second amphiphilic phase consists of polyethoxylated hydrogenated castor oil.

5. The hair care and conditioning preparation as defined in claim 4, wherein the polyethoxylated hydrogenated castor oil consists of hydrogenated castor oil ethoxylated with seven of said ethylene oxide groups.

6. The hair care and conditioning preparation as defined in claim 4, wherein the polyethoxylated hydrogenated castor oil consists of hydrogenated castor oil ethoxylated with 40 of said ethylene oxide groups.

7. The hair care and conditioning preparation as defined in claim 1, further comprising at least one additive substance selected from the group consisting of lecithins, vitamins and antioxidants.

8. The hair care and conditioning preparation as defined in claim 1, containing 84 percent by weight of jojoba oil and 16 percent by weight hydrogenated polyethoxylated castor oil.

9. The hair care and conditioning preparation as defined in claim 1, having the following composition in percent by weight: jojoba oil, 33%; sunflower oil, 32%; avocado oil, 31%; castor oil ethoxylated with 40 of said ethylene oxide groups, 2%; castor oil ethoxylated with 7 of said ethylene oxide groups, 1%; antioxidant, 0.1%; and water, 0.9%.

10. A hair care and conditioning preparation, consisting essentially of from 65 to 98 percent by weight of a first lipophilic phase, from 2 to 33 percent by weight of a second amphiphilic phase and from 0 to 5 percent by weight water,
wherein the first lipophilic phase consists of at least one member selected from the group consisting of jojoba oil, avocado oil, sunflower oil and wheat germ oil;
wherein said second amphiphilic phase consists of at least one amphiphilic substance selected from the group consisting of ethoxylated fatty acids, ethoxylated fatty acid amines and ethoxylated fatty acid amides; and
wherein said ethoxylated fatty acids are fatty acids containing from 6 to 30 carbon atoms which are ethoxylated with from 2 to 200 ethylene oxide groups; said ethoxylated fatty acid amines are fatty acid amines containing from 6 to 30 carbon atoms which are ethoxylated with from 2 to 200 ethylene oxide groups; and said ethoxylated fatty acid amides are fatty acid amides containing from 6 to 30 carbon atoms which are ethoxylated with from 2 to 200 ethylene oxide groups.

11. The hair care and conditioning preparation as defined in claim 10, wherein the second amphiphilic phase is formed by a polyethoxylated hydrogenated castor oil.

12. The hair care and conditioning preparation as defined in claim 11, wherein the polyethoxylated hydrogenated castor oil consists of hydrogenated castor oil ethoxylated with seven of said ethylene oxide groups.

13. The hair care and conditioning preparation as defined in claim 11, wherein the polyethoxylated hydrogenated castor oil consists of hydrogenated castor oil ethoxylated with 40 of said ethylene oxide groups.

14. A method of permanent shaping of hair, said method comprising the steps of:
a) providing a hair care and conditioning preparation consisting essentially of from 65 to 98 percent by weight of a first lipophilic phase, from 2 to 33 percent by weight of a second amphiphilic phase and from 0 to 5 percent by weight water, wherein said first lipophilic phase consists of at least one vegetable-based or animal-based natural oil, and the second amphiphilic phase consists of at least one amphiphilic substance selected from the group consisting of ethoxylated fatty acids, ethoxylated fatty acid amines and ethoxylated fatty acid amides; wherein said ethoxylated fatty acids are fatty acids containing from 6 to 30 carbon atoms which are ethoxylated with from 2 to 200 ethylene oxide groups; said ethoxylated fatty acid amines are fatty acid amines containing from 6 to 30 carbon atoms which are ethoxylated with from 2 to 200 ethylene oxide groups; and said ethoxylated fatty acid amides are fatty acid amides containing from 6 to 30 carbon atoms which are ethoxylated with from 2 to 200 ethylene oxide groups;
b) moving said hair care and conditioning preparation, prior to use, in order to attain an intimate mixture;
c) after the moving of step b), applying said intimate mixture to damp hair as a balancing pre-wrap solution;
d) after an acting time for action of the preparation on the damp hair, rinsing said intimate mixture out of the hair with water; and
e) after the rinsing of step d), applying a permanent shaping composition to the hair to perform the permanent shaping of the hair.

15. The method as defined in claim 14, wherein said first lipophilic phase consists of at least one member selected from the group consisting of jojoba oil, avocado oil, sunflower oil and wheat germ oil; and said second amphiphilic phase consists of polyethoxylated hydrogenated castor oil.

16. The method as defined in claim 14, further comprising addition of a shampoo to said water used in said rinsing.

17. A method of conditioning and caring for hair comprising the steps of:
a) providing a hair care and conditioning preparation consisting essentially of from 65 to 98 percent by weight of a first lipophilic phase, from 2 to 33 percent by weight of a second amphiphilic phase and from 0 to 5 percent by weight water,
wherein said first lipophilic phase consists of at least one vegetable-based or animal-based natural oil, and wherein the second amphiphilic phase consists of at least one amphiphilic substance selected from the group consisting of ethoxylated fatty acids, ethoxylated fatty acid amines and ethoxylated fatty acid amides; wherein said ethoxylated fatty acids are fatty acids containing from 6 to 30 carbon atoms which are ethoxylated with from 2 to 200 ethylene oxide groups; said ethoxylated fatty acid amines are fatty acid amines containing from 6 to 30 carbon atoms which are ethoxylated with from 2 to 200 ethylene oxide groups; and said ethoxylated fatty acid amides are fatty acid amides containing from 6 to 30 carbon atoms which are ethoxylated with from 2 to 200 ethylene oxide groups;
b) moving said hair care and conditioning preparation, prior to use, in order to attain an intimate mixture;
c) adding said intimate mixture to a hair treatment composition to obtain a hair treatment mixture;
d) applying the hair treatment mixture to damp hair; and
e) after an acting time for the hair treatment mixture on the damp hair, rinsing said hair treatment mixture out of the hair with water.

18. The method as defined in claim 17, wherein said first lipophilic phase consists of at least one member selected from the group consisting of jojoba oil, avocado oil, sunflower oil and wheat germ oil; and said second amphiphilic phase consists of polyethoxylated hydrogenated castor oil.

19. The method as defined in claim 17, further comprising allowing said intimate mixture to act on said hair at elevated temperatures.

20. A kit comprising a container containing a hair care and conditioning preparation and another container containing a hair treatment composition;

wherein said hair care and conditioning preparation consists essentially of from 65 to 98 percent by weight of a first lipophilic phase, from 2 to 33 percent by weight of a second amphiphilic phase and from 0 to 5 percent by weight water;

wherein said first lipophilic phase consists of at least one vegetable-based or animal-based natural oil, and said second amphiphilic phase consists of at least one amphiphilic substance selected from the group consisting of ethoxylated fatty acids, ethoxylated fatty acid amines and ethoxylated fatty acid amides;

wherein said ethoxylated fatty acids are fatty acids containing from 6 to 30 carbon atoms which are ethoxylated with from 2 to 200 ethylene oxide groups; said ethoxylated fatty acid amines are fatty acid amines containing from 6 to 30 carbon atoms which are ethoxylated with from 2 to 200 ethylene oxide groups; and said ethoxylated fatty acid amides are fatty acid amides containing from 6 to 30 carbon atoms which are ethoxylated with from 2 to 200 ethylene oxide groups.

* * * * *